United States Patent
Demerson et al.

(10) Patent No.: US 7,683,051 B2
(45) Date of Patent: Mar. 23, 2010

(54) CRYSTALLINE POLYMORPH OF BAZEDOXIFENE ACETATE

(75) Inventors: Christopher Demerson, Kirkland (CA); Silvio Iera, Montreal (CA); Kadum A. Ali, Congers, NY (US)

(73) Assignee: Wyeth, Madison, NJ (US)

( * ) Notice: Subject to any disclaimer, the term of this patent is extended or adjusted under 35 U.S.C. 154(b) by 703 days.

(21) Appl. No.: 11/100,983

(22) Filed: Apr. 6, 2005

(65) Prior Publication Data

US 2005/0227965 A1    Oct. 13, 2005

Related U.S. Application Data

(60) Provisional application No. 60/560,582, filed on Apr. 7, 2004, provisional application No. 60/660,178, filed on Mar. 10, 2005.

(51) Int. Cl.
*A61P 5/30* (2006.01)
*A61K 31/55* (2006.01)
*C07D 403/02* (2006.01)

(52) U.S. Cl. .................... 514/217.08; 540/602
(58) Field of Classification Search ............ 514/217.08; 540/602
See application file for complete search history.

(56) References Cited

U.S. PATENT DOCUMENTS

| | | | |
|---|---|---|---|
| 5,780,497 A | 7/1998 | Miller et al. | |
| 5,880,137 A | 3/1999 | Miller et al. | |
| 5,998,402 A | 12/1999 | Miller et al. | |
| 6,242,605 B1 | 6/2001 | Raveendranath et al. | |
| 6,479,535 B1 | 11/2002 | Pickar et al. | |
| 2002/0031548 A1 | 3/2002 | Benjamin et al. | |
| 2004/0002535 A1 | 1/2004 | Fensome et al. | |
| 2005/0227965 A1 | 10/2005 | Demerson et al. | |

FOREIGN PATENT DOCUMENTS

| | | |
|---|---|---|
| EP | 802183 | 10/1997 |
| EP | 802184 | 10/1997 |
| EP | 1336602 | 8/2003 |
| WO | WO 99/19293 | 4/1999 |
| WO | WO 02/03987 | 1/2002 |

OTHER PUBLICATIONS

Miller, et al., "Design, Synthesis, and Preclinical Characterization of Novel, Highly Selective Indole Estrogens," *J. Med. Chem.* (2001) 44 (11):1654-1657 and supporting information.
Miller, et al., Drugs of the Future (2002) 27(2):117.
Greenberger, et al., "A New Antiestrogen, 2-(4-Hydroxy-phenyl)-3-methyl-1-[4-(2-piperidin-1-yl-ethoxy)-benzyl]-1H-indol-5-ol hydrochloride (ERA-923), Inhibits the Growth of Tamoxifen-sensitive and -resistant Tumors and is Devoid of Uterotropic Effects in Mice and Rats," *Clinical Cancer Research* (2001) 7:3166-3177.
Biskobing, "Novel Therapies for Osteoporosis", Expert Opin Investig Drugs, 12(4):611-621 (2003)—Abstract Only.
Bryn, et al., "Chapter 10: Polymorphs", *Solid-State Chemistry of Drugs, Second Edition*, SSCI, Inc., West Lafayette, IN, pp. 143-231 (1999).
Miller, et al., "Bazedoxifene Acetate *Selective Estrogen Receptor Modulator Treatment and Prevention of Osteoporosis*", Drugs of the Future, 27(2): 117-121, 2002.
Proteau, "Steroid Hormones and Therapeutically Related Compounds", *Wilson and Gisvold's Textbook of* Organic Medical and Pharmaceutical Chemistry, Eleventh Edition, Chapter 23, pp. 767-817 (2004).
"CMU Seed Fund Project on Detection and Control of Pharmaceutical Polymorphism", Carnegie Mellon Department of Physics, http://andrew.cmu.edu/user/suter/polymorph.html, printed Apr. 3, 2008.
Doelker, "Caracteres Physicochimiques des Principes Actifs Leurs Consequences sur la Faisabilite et la Staiblite des Formes Galeniques", Pharma Pratiques, 9(5):399-409 (1999) (English Abstract).
Doelker, "Seance Thematique Modifications Cristallines et Transformations Polymorphes au Cors des Operations Galeniques", Ann Pharm Fr. 60:161-176 (2002) - English Language Abstract.
Jain, et al., "Polymorphism in Pharmacy", Indian Drugs, 23(6):315-329 (1986).
Miller, et al., "Design, Synthesis, and Preclinical Characterization of Novel, Highly Selective Indole Estrogens", J. Med. Chem., 44:1654-1657 (2001).
Otsuka, et al., "Effect of Polymorphic Forms of Bulk Powders on Pharmaceutical Properties of Carbamazepine Granules", Chem. Pharm. Bull., 47(6):852-856 (1999).
Singhal, et al., "Drug Polymorphism and Dosage Form Design: A Practical Perspective", Advanced Drug Delivery Reviews, 56:335-347 (2004).
Ulrich, "Crystallization", in Kirk-Othmer Encyclopedia of Chemical Technology, vol. 8, pp. 95-147, 2002.

*Primary Examiner*—Brenda L. Coleman
(74) *Attorney, Agent, or Firm*—Wilmer Cutler Pickering Hale and Dorr LLP

(57) ABSTRACT

The present invention is directed to a crystalline polymorph of bazedoxifene acetate, compositions containing the same, preparations thereof, and uses thereof.

91 Claims, 4 Drawing Sheets

CRYSTALLINE POLYMORPH OF BAZEDOXIFENE ACETATE

CROSS REFERENCE TO RELATED APPLICATIONS

This application claims the benefit of U.S. Ser. No. 60/560,582, filed Apr. 7, 2004 and U.S. Ser. No. 60/660,178, filed Mar. 10, 2005, the disclosures of each of which are incorporated herein by reference in their entireties.

FIELD OF THE INVENTION

The present invention relates to a crystalline polymorph, designated form A, of the selective estrogen receptor modulator 1-[4-(2-azepan-1-yl-ethoxy)-benzyl]-2-(4-hydroxy-phenyl)-3-methyl-1H-indol-5-ol acetic acid (bazedoxifene acetate).

BACKGROUND OF THE INVENTION

Bazedoxifene acetate (1-[4-(2-azepan-1-yl-ethoxy)-benzyl]-2-(4-hydroxy-phenyl)-3-methyl-1H-indol-5-ol acetic acid), having the chemical formula shown below:

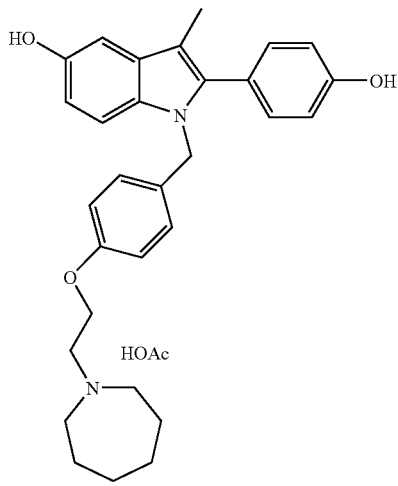

belongs to the class of drugs typically referred to as selective estrogen receptor modulators (SERMs). Consistent with its classification, bazedoxifene demonstrates affinity for estrogen receptors (ER) but shows tissue selective estrogenic effects. For example. bazedoxifene acetate demonstrates little or no stimulation of uterine response in preclinical models of uterine stimulation. Conversely, bazedoxifene acetate demonstrates an estrogen agonist-like effect in preventing bone loss and reducing cholesterol in an ovariectomized rat model of osteopenia. In an MCF-7 cell line (human breast cancer cell line), bazedoxifene acetate behaves as an estrogen antagonist. These data demonstrate that bazedoxifene acetate is estrogenic on bone and cardiovascular lipid parameters and antiestrogenic on uterine and mammary tissue and thus has the potential for treating a number of different disease or disease-like states wherein the estrogen receptor is involved.

U.S. Pat. Nos. 5,998,402 and 6,479,535 report the preparation of bazedoxifene acetate and characterize the salt as having a melting point of 174-178° C. The synthetic preparation of bazedoxifene acetate has also appeared in the general literature. See, for example, Miller et al., *J. Med. Chem.*, 2001, 44, 1654-1657, which reports the salt as a crystalline solid having a melting point of 170.5-172.5° C. Further description of the drug's biological activity has appeared in the general literature as well (e.g. Miller, et al. *Drugs of the Future*, 2002, 27(2), 117-121).

It is well known that the crystalline polymorph form of a particular drug is often an important determinant of the drug's ease of preparation, stability, solubility, storage stability, ease of formulation and in vivo pharmacology. Polymorphic forms occur where the same composition of matter crystallizes in a different lattice arrangement resulting in different thermodynamic properties and stabilities specific to the particular polymorph form. In cases where two or more polymorph substances can be produced, it is desirable to have a method to make both polymorphs in pure form. In deciding which polymorph is preferable, the numerous properties of the polymorphs must be compared and the preferred polymorph chosen based on the many physical property variables. It is entirely possible that one polymorph form can be preferable in some circumstances where certain aspects such as ease of preparation, stability, etc are deemed to be critical. In other situations, a different polymorph maybe preferred for greater solubility and/or superior pharmacokinetics.

Because improved drug formulations, showing, for example, better bioavailability or better stability are consistently sought, there is an ongoing need for new or purer polymorphic forms of existing drug molecules. The polymorph of bazedoxifene acetate described herein helps meet these and other needs.

SUMMARY OF THE INVENTION

Figure 1:
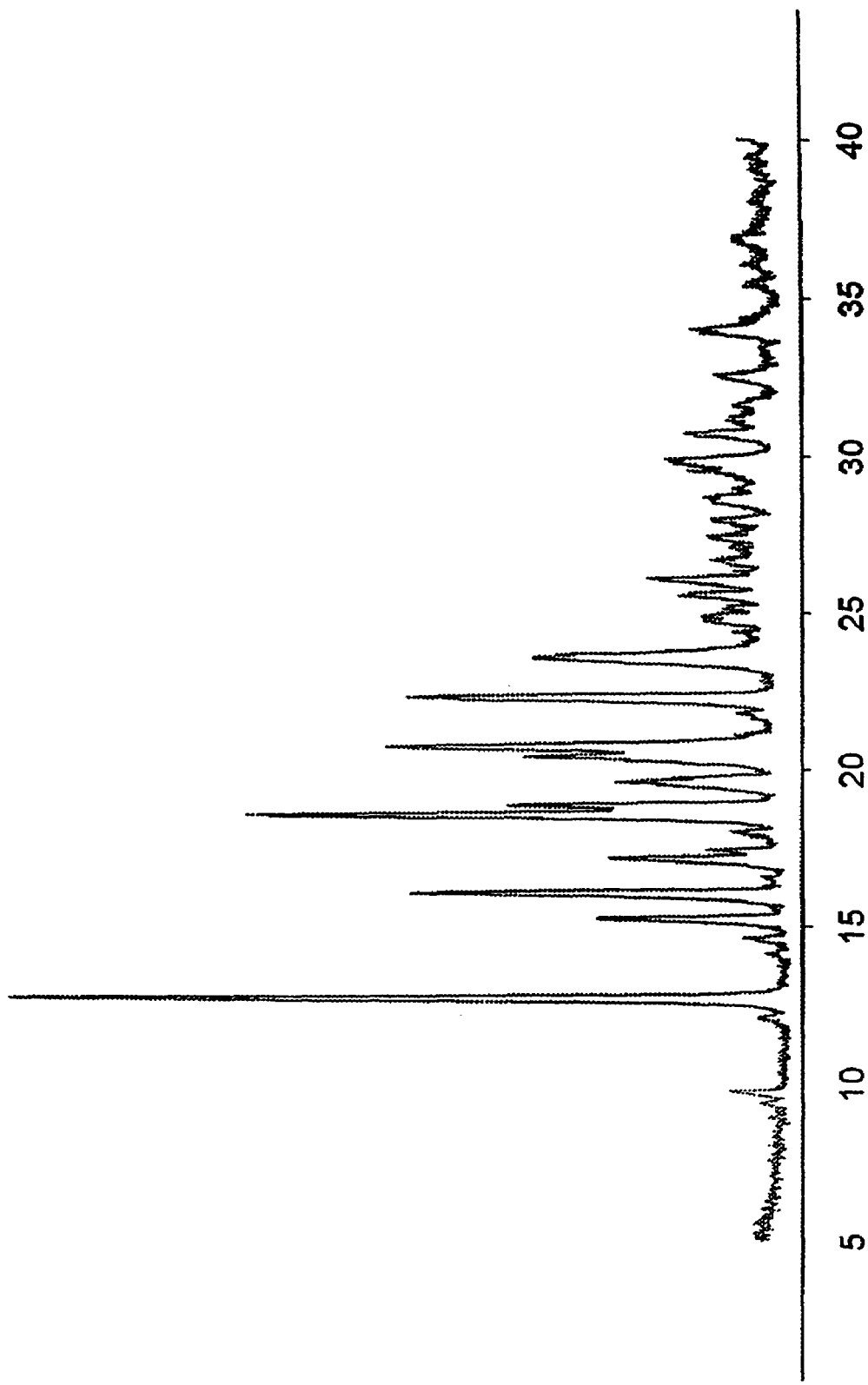
FIG. 1 depicts a powder X-ray diffraction pattern of bazedoxifene acetate form A polymorph, where the diffraction angle (2θ) ranges from 5° to 4° with a step of 0.02°.

The present invention provides a crystalline polymorph (form A) of bazedoxifene acetate characterized according to the powder X-ray diffraction data, IR data, and DSC data provided herein.

The present invention further provides compositions containing polymorphic form A of bazedoxifene acetate.

The present invention further provides a method of preparing bazedoxifene acetate polymorphic form A comprising:
a) reacting hexamethyleneimino benzyloxyindole with a hydrogenating reagent in a solvent and optionally in the presence of a hydrogenation catalyst for a time and under conditions suitable for forming a reaction mixture comprising bazedoxifene free base;
b) treating the reaction mixture with acetic acid for a time and under conditions suitable for forming bazedoxifene acetate polymorphic form A.

The present invention further provides a method of treating a mammal having a disease or syndrome associated with estrogen deficiency or excess of estrogen comprising administering to said mammal a therapeutically effective amount of form A polymorph of bazedoxifene acetate.

The present invention further provides a method of treating a mammal having a disease or disorder associated with proliferation or abnormal development of endometrial tissues comprising administering to said mammal a therapeutically effective amount of form A polymorph of bazedoxifene acetate.

The present invention further provides a method of lowering cholesterol in a mammal comprising administering to said mammal a therapeutically effective amount of form A polymorph of bazedoxifene acetate.

The present invention further provides a method of inhibiting bone loss or breast cancer in a mammal comprising administering to the mammal a therapeutically effective amount of form A polymorph of bazedoxifene acetate.

The present invention further provides a method of treating a postmenopausal woman for one or more vasomotor disturbances, such as hot flush, comprising administering to the postmenopausal woman a therapeutically effective amount of form A polymorph of bazedoxifene acetate.

The present invention further provides the crystalline polymorph form A of bazedoxifene acetate prepared by any of the methods described herein.

DETAILED DESCRIPTION

The present invention provides an anhydrous, non-solvated crystalline polymorph of bazedoxifene acetate, referred to herein as form A, which can be identified by one or more solid state analytical methods. For example, form A can be identified by its powder X-ray diffraction pattern which is provided in FIG. 1. Powder X-ray diffraction data consistent with form A is provided in Table 1 below.

TABLE 1

| Degree (2θ) | Intensity, Counts Per Second (CPS) |
|---|---|
| 9.8 | 180 |
| 12.7 | 3111 |
| 15.2 | 683 |
| 16.0 | 1347 |
| 17.1 | 591 |
| 17.4 | 220 |
| 18.5 | 1964 |
| 18.8 | 970 |
| 19.6 | 482 |
| 20.4 | 894 |
| 20.7 | 1440 |
| 22.3 | 1373 |
| 23.5 | 822 |
| 24.9 | 145 |
| 25.6 | 231 |
| 26.1 | 346 |
| 27.4 | 147 |
| 28.0 | 152 |
| 28.7 | 153 |
| 29.6 | 202 |
| 29.9 | 307 |
| 30.7 | 268 |

In some embodiments, the crystalline polymorph (form A) of bazedoxifene acetate is characterized by a powder X-ray diffraction pattern having characteristic peaks, in terms of 2θ, at about 12.7° and about 18.5°. In further embodiments, the powder X-ray diffraction pattern further includes characteristic peaks, in terms of 2θ, at about 16.0°, about 20.7°, and about 22.3°. In further embodiments, the powder X-ray diffraction pattern of form A includes 5 or more characteristic peaks, in terms of 2θ, selected from about 9.8°, about 12.7°, about 15.2°, about 16.0°, about 17.1°, about 17.4°, about 18.5°, about 18.8°, about 19.6°, about 20.4°, about 20.7°, about 22.3°, about 23.5°, about 24.9° about 25.6°, about 26.1°, about 27.4°, about 28.0°, about 28.7°, about 29.6°, about 29.9°, and about 30.7°. In yet further embodiments, form A is characterized by a powder X-ray diffraction pattern substantially as shown in FIG. 1. The relative intensities of the peaks can vary, depending upon the sample preparation technique, the sample mounting procedure and the particular instrument employed. Moreover, instrument variation and other factors can affect the 2-theta values. Therefore, the XRPD peak assignments can vary by plus or minus about 0.2°.

Figure 2:
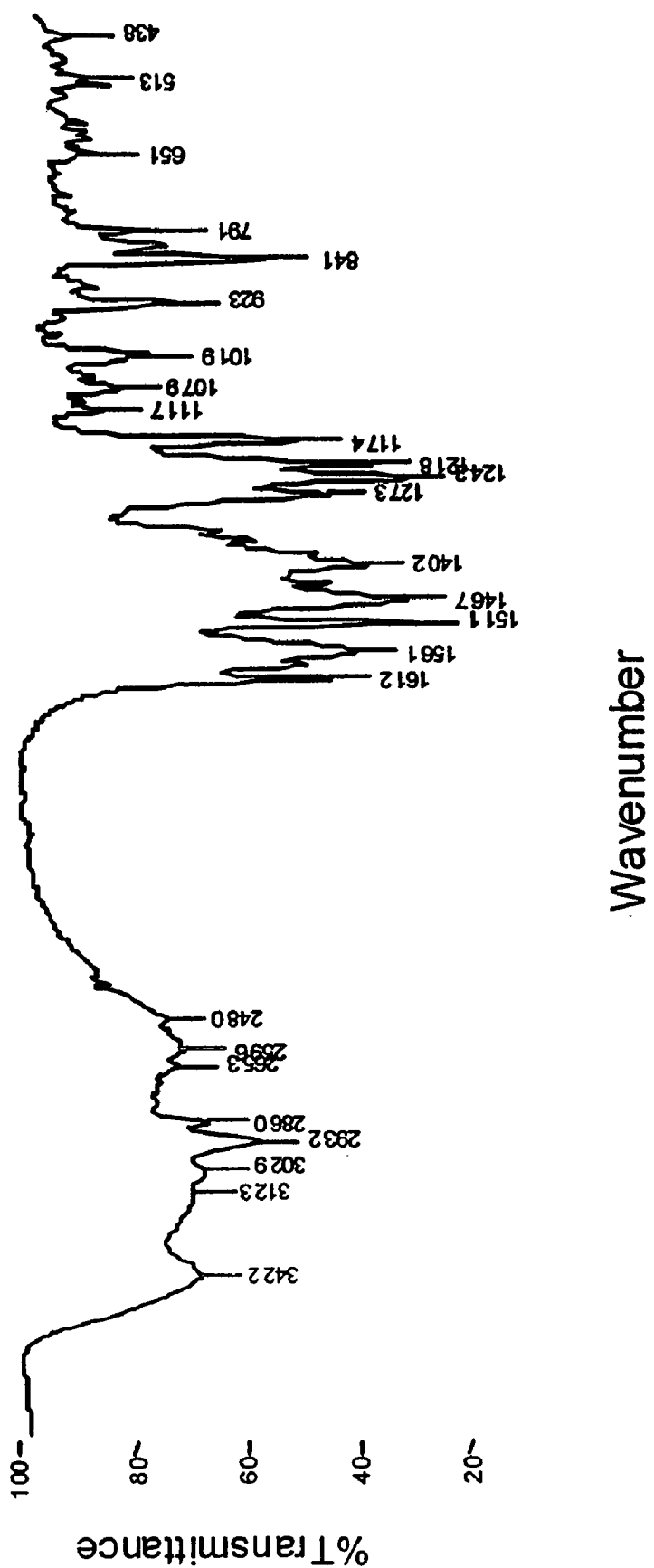
FIG. 2 depicts an IR spectrum of bazedoxifene acetate form A polymorph in KBr pellet.

Form A can also be identified by its characteristic infrared (IR) absorption spectrum such as provided in FIG. 2. In some embodiments, form A is characterized by an infrared spectrum in KBr having one or more characteristic peaks selected from about 1511, about 1467, and about 1242 cm$^{-1}$.

Figure 3:
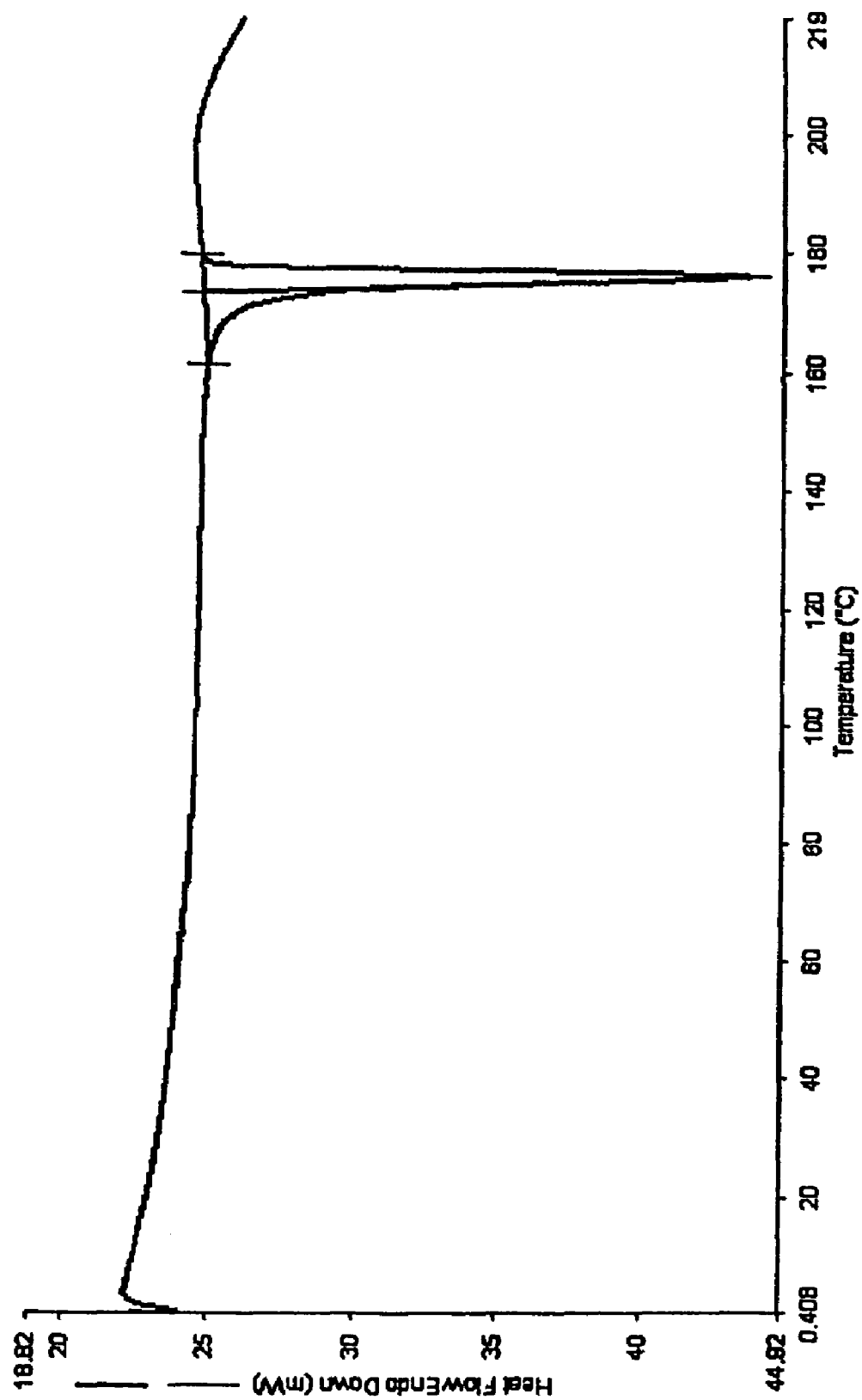
FIG. 3 depicts a differential scanning calorimetric (DSC) trace of bazedoxifene acetate form A polymorph.

Form A can also be identified by its characteristic differential calorimeter scanning (DSC) trace such as shown in FIG. 3. In some embodiments, form A is characterized by a DSC trace showing a maximum at about 176° C. For DSC, it is known that the temperatures observed will depend upon the rate of temperature change as well as sample preparation technique and the particular instrument employed. Thus, the values reported herein relating to DSC thermograms can vary by plus or minus about 4° C.

Baxedoxifene acetate polymorphic form A is readily distinguishable from other crystalline polymorphs, such as the less soluble form B. Sample data for several physical properties are compared for form A and form B polymorphs below in Table 2.

TABLE 2

| Measurement | Form A | Form B |
|---|---|---|
| Melting Point | 176° C. | 181° C. |
| Heat of Fusion | 94.6 J/G | 108.4 J/G |
| Solubility-Water | 0.49 mg/mL | 0.23 mg/mL |
| Solubility-Org (EtOH/EtOAc/Tol) | 24.5 mg/mL | 12.4 mg/mL |
| Intrinsic Dissolution Rate | 0.125 mg/cm$^2$-min | 0.09 mg/cm$^2$-min |
| DSC | Single Melting Endotherm 176.1° C. | Single Melting Endotherm 181.1° C. |
| TGA | Similar | Similar |
| X-Ray Powder | 12.7°, 16.0°, 18.5°, 20.7°, 22.3° (2θ) | 13.3°, 20.8°, 21.6°, 25.0° (2θ) |
| Raman/IR | 1511, 1467 cm$^{-1}$ | 1513, 1449, 1406 cm$^{-1}$ |

As can be seen in Table 2, the two crystalline polymorphs have discernable physical and spectroscopic characteristics. Form A appears to have higher solubility in aqueous and organic solvent systems than does form B, which is advantageous in particular formulations or doses where the solubility of the particular composition is of concern. For example, higher solubility can contribute to better biological absorption and distribution of the drug, as well as facilitate formulation in liquid carriers.

Form A can be prepared by, for example, deprotecting hexamethylene benzyloxyindole (see, e.g., U.S. Pat. No. 5,998,402) by hydrogenolysis in a solvent containing an alcohol (e.g., ethanol) in the presence of a hydrogenation catalyst (e.g., 10% palladium on charcoal; Pd/C 10%). Hydrogenolysis can be carried out for any length of time and is typically carried out until the reaction is substantially complete as can be monitored by HPLC or any other suitable technique. The catalyst can be subsequently removed by filtration and an antioxidant (e.g., ascorbic acid) added to inhibit possible oxidative degradation of the hydrogenated product. Example suitable weight ratios of solvent to hexamethylene benzyloxyindole include, for example, about 10:1 to about 2:1, about 8:1 to about 4:1, or about 6:1 to about 7:1.

Acetic acid can be added to the hydrogenated product (bazedoxifene free base), forming the acetate salt. Suitable amounts of acetic acid are typically sufficient to convert all free base present in the reaction mixture to salt form. Accordingly, one or more equivalents of acetic acid (relative to amount of hexamethylene benzyloxyindole starting material) can be added. In some embodiments, about 1 to about 2 equivalents of acetic acid are added. The full desired amount of acetic acid can be added in one or multiple portions. Crystalline product typically precipitates out of solution upon addition of the acetic acid and can be recrystallized from an alcohol-containing solvent according to routine methods.

Suitable alcohols used in the solvents of the preparation and recrystallization procedures above can include, for example, methanol, ethanol, isopropanol, mixtures thereof and the like. In some embodiments, the alcohol is ethanol which can be optionally denatured with about 1-10% v/v toluene, about 1-10% v/v hexanes, about 1-10% v/v ethyl acetate, and the like. In further embodiments, the reaction solvent and/or recrystallizing solvent is ethanol containing 5% (by volume) ethyl acetate. In further embodiments, the solvent is ethanol.

The steps involved in the preparation of form A can be carried out at any suitable temperature, such as at or below about 25, about 20, or about 15° C. For example, hydrogenation can be carried out at ambient temperature such as 25° C. Addition of acetic acid can be carried out at about 20° C or lower. Reaction mixture containing bazedoxifene acetate can be maintained for any length of time (e.g., at least about 1 hr, at least about 2 hrs, at least about 6 hr, or at least about 12 hrs) at a temperature from about −20 to about 20° C. In some embodiments, the reaction mixture is held for at least about 2 hours at 20° C. In some embodiments, the reaction mixture is held for at least about 2 hours at 0° C.

The proportion of form B, in a composition containing a mixture of form A and form B, can be increased according to the following methods. For example, form B can comprise less than about 10%, less than about 20%, less than about 30%, or less than about 40% by weight of total bazedoxifene acetate in the starting composition. Proportion of form B can be increased by combining solvent containing an alcohol with the starting composition and maintaining the resulting mixture at or above a temperature of about 25° C (e.g., about 25 to about 60, about 25 to about 40, or about 25 to about 30° C.) for a length of time suitable for increasing the proportion of form B in the composition. Solvent can be provided in an amount sufficient to dissolve substantially all or less than all of the bazedoxifene acetate starting material forming homogenous or heterogeneous mixtures, respectively. The solvent can be provided in a weight ratio of total solvent to amount of bazedoxifene starting material of, for example, about 5:1, about 3:1, about 2:1, or about 1:1.

In some embodiments, the mixture of bazedoxifene acetate and solvent is heated to reflux temperature, such as for several hours (e.g., about 1 to about 3 hours) then slowly cooled in a stepwise fashion. For example, the mixture can be cooled to about 45 to about 55° C. (e.g., about 50° C.) over the course of a first time period and then cooled to about 10 to about 30° C. (e.g., about 20° C.) over the course of a second time period.

First, second, and any additional time periods can last for several hours such as from about 1 to about 5 hours or about 1 to about 3 hours. In some embodiments, the first time period is about 1 hour and the second time period is about 3 hours. The mixture can further be maintained at the cooled temperature (e.g, about 10 to about 30° C.) for an additional time period sufficient for precipitation of product. The additional time period can be, for example, 2 hours to about 24 hours, about 8 to about 18 hours, or about 13 hours.

In some embodiments, form A can be prepared by crystallizing bazedoxifene acetate from a solution comprising an alcohol wherein the solution is maintained at a temperature below about 20° C., below about 10° C., or below about 5° C. The alcohol can comprise methanol, ethanol, n-propanol, isopropanol, mixtures thereof and the like. In some embodiments, the alcohol includes ethanol.

Processes for preparing form A can also include seeding of solutions containing bazedoxifene acetate with form A seed crystals, and processes for preparing form B can also include seeding of solutions containing bazedoxifene acetate with from B seed crystals.

An example preparation of form A is provided in Example 1. An example preparation of form B is provided in Example 2.

The methods for preparation of form A provided herein can result in substantially pure form A (e.g., compositions containing less than about 10%, less than about 5%, or less than about 3% of form B) as well as mixtures enriched in form A (e.g., greater than about 50% form A relative to form B). Accordingly, the present invention further provides compositions containing form A. In some embodiments, at least about 50%, at least about 70%, at least about 80%, at least about 90%, at least about 95%, at least about 97%, at least about 98.0%, at least about 98.1%, at least about 98.2%, at least about 98.3%, at least about 98.4%, at least about 98.5%, at least about 98.6%, at least about 98.7%, at least about 98.8%, at least about 98.9%, at least about 99.0%, at least about 99.1%, at least about 99.2%, at least about 99.3%, at least about 99.4%, at least about 99.5%, at least about 99.6%, at least about 99.7%, at least about 99.8%, or at least about 99.9% by weight of total bazedoxifene acetate in a composition is present as form A. In further embodiments, compositions of the present invention consist essentially of bazedoxifene acetate where at least about 95%, at least about 97%, at least about 98.0%, at least about 98.1%, at least about 98.2%, at least about 98.3%, at least about 98.4%, at least about 98.5%, at least about 98.6%, at least about 98.7%, at least about 98.8%, at least about 98.9%, at least about 99.0%, at least about 99.1%, at least about 99.2%, at least about 99.3%, at least about 99.4%, at least about 99.5%, at least about 99.6%, at least about 99.7%, at least about 99.8%, or at least about 99.9% by weight of the bazedoxifene acetate is present in the composition as form A. In some embodiments, the remainder bazedoxifene acetate is present as form B or as amorphous material. Respective amounts of polymorphic forms of bazedoxifene acetate in a composition can be determined by any suitable spectroscopic method, such as X-ray powder diffraction or DSC.

The present invention further provides compositions comprising the polymorph of the invention (Form A) and Form B. In some embodiments, the composition comprises about 70 to about 90% by weight of Form A and about 10 to about 30% by weight of Form B, about 75 to about 85% by weight of Form A and about 15 to about 25% by weight of Form B, 78 to about 92% by weight of Form A and about 18 to about 22% by weight of Form B, or about 80% by weight of Form A and about 20% by weight of Form B.

The present invention further provides compositions comprising bazedoxifene acetate wherein about 70% to about 90% by weight of total bazedoxifene acetate in the composition is present as the polymorph of the invention (Form A) and about 10 to about 30% by weight of total bazedoxifene acetate in the composition is present as Form B, or wherein about 75% to about 85% by weight of total bazedoxifene acetate in the composition is present as the polymorph of the invention (Form A) and about 15 to about 25% by weight of total bazedoxifene acetate in the composition is present as Form B, or wherein about 78% to about 82% by weight of total bazedoxifene acetate in the composition is present as the polymorph of the invention (Form A) and about 18 to about 22% by weight of total bazedoxifene acetate in the composition is present as Form B, or wherein about 80% by weight of total bazedoxifene acetate in the composition is present as the polymorph of the invention (Form A) and about 20% by weight of total bazedoxifene acetate in the composition is present as Form B.

The compositions containing Forms A and B can be prepared by any suitable method include admixture of substantially pure Forms A and B made, for example, according to any of the processes provided herein.

Methods

As described in U.S. Pat. No. 5,998,402, bazedoxifene and salts thereof are selective estrogen agonists with affinity for the estrogen receptor. Unlike other types of estrogen agonists, bazedoxifene and salts thereof are antiestrogenic in the uterus and can antagonize the trophic effects of estrogen agonists in uterine tissues. Accordingly, polymorphs of bazedoxifene acetate and compositions containing the same can find many uses related to treating disease states or syndromes associated with an estrogen deficiency or an excess of estrogen. The polymorph can also be used in methods of treatment for diseases or disorders which result from proliferation or abnormal development, actions or growth of endometrial or endometrial-like tissues.

The present polymorphic form of bazedoxifene acetate has the ability to behave like an estrogen agonist by lowering cholesterol and inhibiting bone loss. Accordingly, the polymorph is useful for treating many maladies which result from estrogen effects and estrogen excess or deficiency including osteoporosis, prostatic hypertrophy, male pattern baldness, vaginal and skin atrophy, acne, dysfunctional uterine bleeding, endometrial polyps, benign breast disease, uterine leiomyomas, adenomyosis, ovarian cancer, infertility, breast cancer, endometriosis, endometrial cancer, polycystic ovary syndrome, cardiovascular disease, contraception, Alzheimer's disease, cognitive decline and other CNS disorders, as well as certain cancers including melanoma, prostrate cancer, cancers of the colon, CNS cancers, among others. Additionally, these polymorphs can be used for contraception in premenopausal women, as well as hormone replacement therapy in post-menopausal women (such as for treating vasomotor disturbances such as hot flush) or in other estrogen deficiency states where estrogen supplementation would be beneficial. It can also be used in disease states where amenorrhea is advantageous, such as leukemia, endometrial ablations, chronic renal or hepatic disease or coagulation diseases or disorders.

The polymorph of the invention can also be used in methods of inhibiting bone loss. Bone loss often results from an imbalance in an individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using these polymorphs in individuals with bone fractures, defective bone structures, and those receiving bone-related surgeries and/or the implantation of prosthesis. In addition to the problems described above, the polymorph can be used in treatments for osteoarthritis, hypocalcemia, hypercalcemia, Paget's disease, osteomalacia, osteohalisteresis, multiple myeloma and other forms of cancer having deleterious effects on bone tissues.

Methods of treating the diseases and syndromes listed herein are understood to involve administering to an individual in need of such treatment a therapeutically effective amount of the polymorph of the invention, or composition containing the same. As used herein, the term "treating" in reference to a disease is meant to refer to preventing, inhibiting and/or ameliorating the disease.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting or slowing further development of the pathology and/or symptomatology); and (3) ameliorating the disease; for example, ameliorating a disease, condition or disorder in an individual that is experiencing or displaying the pathology or symptomatology of the disease, condition or disorder (i.e., reversing the pathology and/or symptomatology).

Dosage and Formulation

The invention also includes pharmaceutical compositions utilizing one or more of the present polymorphs along with one or more pharmaceutically acceptable carriers, excipients, etc.

Formulations of bazedoxifene acetate form A include therapeutically effective amounts that can be given in daily doses ranging from 0.1 mg to 1000 mg to a person in need. Example dose ranges vary from 10 mg/day to about 600 mg/day or from 10 mg/day to about 60 mg/day. The dosing can be either in a single dose or two or more divided doses per day. Such doses can be administered in any manner that facilitates the compound's entry into the bloodstream including orally, via implants, parenterally (including intravenous, intraperitoneal, and subcutaneous injection), vaginally, rectally, and transdermally.

In some embodiments, the formulations are administered transdermally which includes all methods of administration across the surface of the body and the inner linings of body passages including epithelial and mucosal tissues. Such administration may be in the form of a lotion, cream, colloid, foam, patch, suspension, or solution.

Oral formulations containing the present polymorph can comprise any conventionally used oral forms, including tablets, capsules, buccal forms, troches, lozenges and oral liquids, suspensions or solutions. Capsules may contain mixtures of the crystalline form A in the desired percentage together any other polymorph(s) of bazedoxifene acetate or amorphous bazedoxifene acetate. Capsules or tablets of the desired crystalline form of the desired percentage composition may also be combined with mixtures of other active compounds or inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Tablet formulations can be made by conventional compression, wet granulation, or dry granulation methods and utilize pharmaceutically acceptable diluents (fillers), binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations used herein can utilize standard delay or time release formulations or spansules. Suppository formulations can be made from traditional materials, including cocoa butter, with or without the addition of waxes to alter the suppositories melting point, and glycerin. Water soluble suppository bases, such as polyethylene glycols of various molecular weights, can also be used.

Example excipient systems suitable for preparing formulations of the present polymorph include one or more fillers, disintegrants, and lubricants.

The filler component can be any filler component known in the art including, but not limited to, lactose, microcrystalline cellulose, sucrose, mannitol, calcium phosphate, calcium carbonate, powdered cellulose, maltodextrin, sorbitol, starch, or xylitol.

Disintegrants suitable for use in the present formulations can be selected from those known in the art, including pregelatinized starch and sodium starch glycolate. Other useful disintegrants include croscarmellose sodium, crospovidone, starch, alginic acid, sodium alginate, clays (e.g. veegum or xanthan gum), cellulose floc, ion exchange resins, or effervescent systems, such as those utilizing food acids (such as citric acid, tartaric acid, malic acid, fumaric acid, lactic acid, adipic acid, ascorbic acid, aspartic acid, erythorbic acid, glutamic acid, and succinic acid) and an alkaline carbonate component (such as sodium bicarbonate, calcium carbonate, magnesium carbonate, potassium carbonate, ammonium carbonate, etc.). The disintegrant(s) useful herein can comprise from about 4% to about 40% of the composition by weight, preferably from about 15% to about 35%, more preferably from about 20% to about 35%.

The pharmaceutical formulations can also contain an antioxidant or a mixture of antioxidants, such as ascorbic acid. Other antioxidants which can be used include sodium ascorbate and ascorbyl palmitate, preferably in conjunction with an amount of ascorbic acid. An example range for the antioxidant(s) is from about 0.5% to about 15% by weight, most preferably from about 0.5% to about 5% by weight.

An example oral formulation contains the present polymorph and the following excipient systems:

a) a filler and disintegrant together comprising from about 5% to about 82% by weight (wght) of the total formulation, preferably between about 30% and about 80% of the formulation, wherein from about 4% to about 40% by weight of the total formulation comprises one or more pharmaceutically acceptable disintegrants; and b) a lubricant comprising from about 0.2% to about 10% of the composition (wght), such as selected from the group of magnesium stearate or other metallic stearates (e.g. calcium stearate or zinc stearate), fatty acid esters (e.g. sodium stearyl fumarate), fatty acids (e.g. stearic acid), fatty alcohols, glyceryl behenate, mineral oil, parraffins. hydrogenated vegetable oils, leucine, polyethylene glycols, metallic lauryl sulfates and sodium chloride.

A further excipient system can comprise:

a) filler and disintegrant together comprising from about 5.4% to about 89%, by weight or preferably from about 32.5% to about 87% by weight; and b) lubricant comprising from about 0.22% to about 10.9% by weight.

The excipient systems can also optionally utilize pharmaceutically acceptable wetting agents, glidants and antioxidants. Such systems can comprise:

a) a filler and disintegrant together comprising from about 5% to about 82% by weight (wght) of the total formulation, preferably between about 30% and about 80% of the formulation, wherein from about 4% to about 40% by weight of the total formulation comprises one or more pharmaceutically acceptable disintegrants;

b) optionally, a wetting agent comprising from about 0.2 to about 5% of the composition (wght), such as selected from the group of sodium lauryl sulfate, polyoxyethylene sorbitan fatty acid esters, polyoxyethylene alkyl ethers, sorbitan fatty acid esters, polyethylene glycols, polyoxyethylene castor oil derivatives, docusate sodium, quaternary ammonium compounds, sugar esters of fatty acids and glycerides of fatty acids;

c) a lubricant comprising from about 0.2% to about 10% of the composition (wght), such as selected from the group of magnesium stearate or other metallic stearates (e.g. calcium stearate or zinc stearate), fatty acid esters (e.g. sodium stearyl fumarate), fatty acids (e.g. stearic acid), fatty alcohols, glyceryl behenate, mineral oil, parraffins, hydrogenated vegetable oils, leucine, polyethylene glycols, metallic lauryl sulfates and sodium chloride; and d) optionally, a glidant comprising from about 0.1% to about 10% (wght) of the final composition, the glidant selected from those known in the art, including from the group of silicon dioxide, talc, metallic stearates, calcium silicate, or metallic lauryl sulfates.

Further excipient systems, according to the present invention, can include, by weight:

a) a filler and disintegrant together comprising between about 54% and about 80% of the formulation, with the disintegrant agent(s) therein comprising from about 4% to about 40% by weight of the overall formulation;

b) a wetting agent comprising between about 0.55% and about 2.5% of the formulation;

c) a lubricant comprising between about 0.2% and about 5.5% of the formulation; and d) a glidant comprising between about 0.1% and about 5.0% of the formulation.

The excipient systems above can also optionally contain an antioxidant component, e.g., ascorbic acid, at a concentration of from about 0.5% to about 5.0% by weight.

Among further excipient systems of this invention are those comprising:

a) a filler and disintegrant together comprising between about 50% and about 87% of the formulation, where the disintegrant(s) therein comprises from about 25% to about 35% of the formulation, by weight;

b) a wetting agent comprising between about 0.55% and about 2.7% of the formulation;

c) a lubricant comprising between about 0.2% and about 5.5% of the formulation;

d) a glidant comprising between about 0.1% and about 5.5% of the formulation; and e) an antioxidant component, such as ascorbic acid, in an amount of from about 0.5% to about 5.5% by weight.

The percentages listed above for the filler, disintegrant, lubricant and other components are based on final pharmaceutical composition. The remaining percentage of the final composition is comprised of the active pharmacological agent(s) and optionally a pharmaceutically acceptable surface covering, such as a coating or capsule, as described herein. In some embodiments of this invention, the active pharmacological agent(s) comprise from about 0.5% to about 20%, by weight, of the final composition, more preferably from about 1% to about 5%, and the coating or capsule comprises up to about 8%, by weight, of the final composition.

The formulations described herein can be used in an uncoated or non-encapsulated solid form. In some embodiments, the pharmacological compositions are optionally coated with a film coating, for example, comprising from about 0.3% to about 8% by weight of the overall composition. Film coatings useful with the present formulations are known in the art and generally consist of a polymer (usually a cellulosic type of polymer), a colorant and a plasticizer. Additional ingredients such as wetting agents, sugars, flavors, oils and lubricants may be included in film coating formulations to impart certain characteristics to the film coat. The compositions and formulations herein may also be combined and processed as a solid, then placed in a capsule form, such as a gelatin capsule.

Pharmaceutical compositions of bazedoxifene acetate can be formulated with steroidal estrogens, such as conjugated estrogens, USP. The amount of bazedoxifene acetate used in the formulation can be adjusted according to the particular polymorph form or ratio of polymorph forms used, the amount and type of steroidal estrogen in the formulation as well as the particular therapeutic indication being considered. In general, the bazedoxifene acetate of defined polymorphic composition ratio can be used in an amount sufficient to antagonize the effect of the particular estrogen to the level desired. The dose range of conjugated estrogens can be from about 0.3 mg to about 2.5 mg, about 0.3 mg to about 1.25 mg, or about 0.3 mg to about 0.625 mg. An example range for amount of bazedoxifene acetate in a combination formulation is about 10 mg to about 40 mg. For the steroidal estrogen mestranol, a daily dosage can be from about 1 μG to about 150 μG, and for ethynyl estradiol a daily dosage of from about 1 μG to about 300 μG can be used. In some embodiments, the daily dose is between about 2 μG and about 150 μG.

In order that the invention disclosed herein may be more efficiently understood, examples are provided below. It should be understood that these examples are for illustrative purposes only and are not to be construed as limiting the invention in any manner.

EXAMPLE

Example 1

Preparation of Bazedoxifene Acetate Form A Polymorph

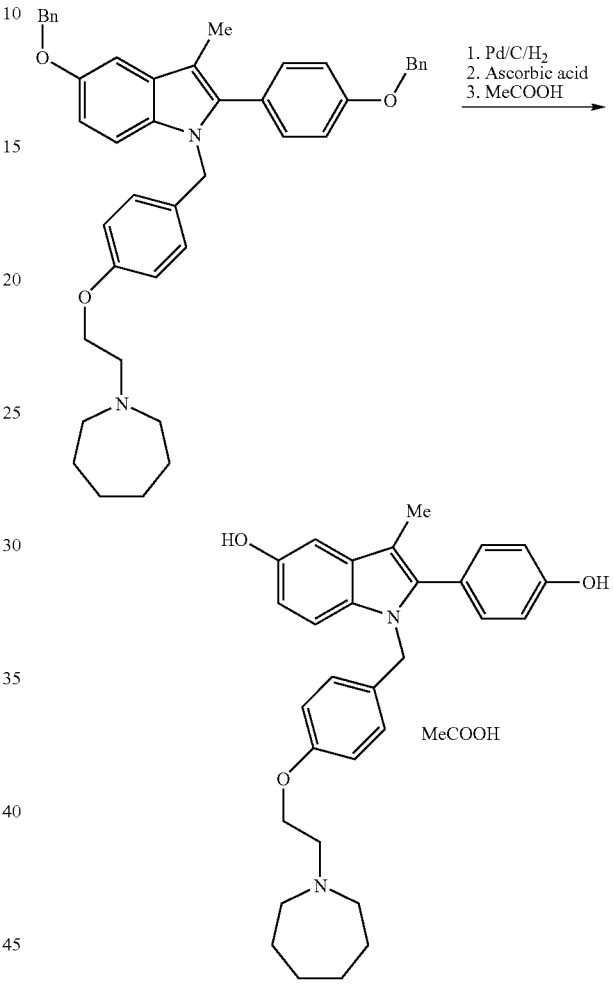

A 2 gal hydrogenation vessel with agitator was charged with hexamethyleneimino benzyloxyindole (250 g, 0.3841 mol; see U.S. Pat. No. 5,998,402 for a preparation), ethanol (denatured with 5% by volume ethyl acetate) (1578 g, 2000 mL), and palladium on carbon 10% (25 g). The reactants were hydrogenated at 25° C. and 50 psi for 20 hours. Reaction progress was monitored by HPLC (Column: CSC-S ODS 2, 25 cm; Mobile phase: 20% 0.02 M $NH_4H_2PO_4$ (2 mL TEA/L, pH=3) and 80% MeCN; Flow: 2 mL/min; Detector: 220 nm). The reaction was considered complete when less than 1% of either the hexamethyleneimino benzyloxyindole (18.2 min retention time) or mono-debenzylated derivative thereof (5.1 min retention time) was detected.

The mixture was filtered through a cartridge which was subsequently rinsed with ethanol (denatured with 5% by volume ethyl acetate) (2×198 g, 2×250 mL). The filtrate was transferred to a 5 L multi-neck flask with agitator charged with L-ascorbic acid (2.04 g, 0.0116 mols) under nitrogen. Acetic acid (34.6 g, 0.5762 moles) was added at 20° C. while stirring. The resulting reaction mixture was stirred for 2 hours (pH was about 5 and crystallization began within about 10 minutes of addition of acetic acid). The reaction mixture was then cooled to 0° C. and maintained at this temperature for 2 hours. The resulting solid was collected by filtration on a Buchner funnel and washed with ethanol (denatured with 5% by volume ethyl acetate) (2×150 g, 2×190 mL) at 0° C.

The solid product was further purified by charging a 3 L multineck flask (with agitator, thermometer, and condenser under nitrogen) with the filtered solid, ethanol (denatured with 5% by volume ethyl acetate) (1105 g, 1400 mL), and L-ascorbic acid (1.73 g, 0.01 mols). The resulting mixture was heated to 75° C. and cooled to 20° C. over the course of 2 hours. The resulting suspension was further cooled to 0° C. and held at this temperature for 2 hours. The resulting solid product was collected by filtration with a Buchner funnel and washed with ethanol (denatured with 5% by volume ethyl acetate) (2×79 g, 2×100 mL) at 0° C. The product was dried in vacuo at 60° C., 5 mm Hg for 24 hours giving 151.3 g bazedoxifene acetate form A (74.2% yield).

Example 2

Preparation of Bazedoxifene Acetate Form B from Form A

To a stirred solution of 594 g of ethanol (denatured with 5% of acetone and with 3% of cyclohexane) and 184 g of ethyl acetate, 400 g of bazedoxifene acetate form A were added under nitrogen (e.g., see Example 1). The heterogeneous mixture was kept at 30° C. and stirred overnight under nitrogen.

The completion of the crystalline transformation was determined by DSC analysis. The mixture was cooled to 0° C. and stirred for 2 hrs under nitrogen. The product was filtered, washed with a mixture of denatured ethanol and ethyl acetate as above and dried overnight at 60° C. under vacuum giving 391 g (97.7% yield) of bazedoxifene acetate form B polymorph.

A substantially identical result was obtained using absolute ethanol or ethanol denatured with 5% toluene.

Example 3

X-Ray Powder Diffraction (XRPD)

XRPD analyses (see, e.g., FIG. 1) were carried out on a (Scintag X2) X-ray powder diffractometer using Cu K α radiation. The instrument was equipped with tube power, and amperage was set at 45 kV and 40 mA. The divergence and scattering slits were set at 1° and the receiving slit was set at 0.2 mm. A theta-two theta continuous scan at 3°/min (0.4 sec/0.02° step) from 3 to 40°2θ was used.

Example 4

Infrared (IR) Spectroscopy

IR spectra (e.g., see FIG. 2) were acquired as follows. Samples were prepared as potassium bromide (KBr) discs (or pellets). A small amount of each sample (about 3 mg) was ground in a hard surface mortar until glossy in appearance. One half gram (0.5 g) of KBr was added to the sample and the mixture was continuously ground until well mixed. The mixture was then transferred to a die and pressed into a disc using a hydraulic press.

The IR spectrum of FIG. 2 was obtained using a DIGILAB EXCALIBUR Series FTS-4000 FT-IR Spectrometer operated at 4 cm$^{-1}$ resolution and 16 scans between 400-4000 cm$^{-1}$.

Example 5

Differential Scanning Calorimetry (DSC)

Figure 4:
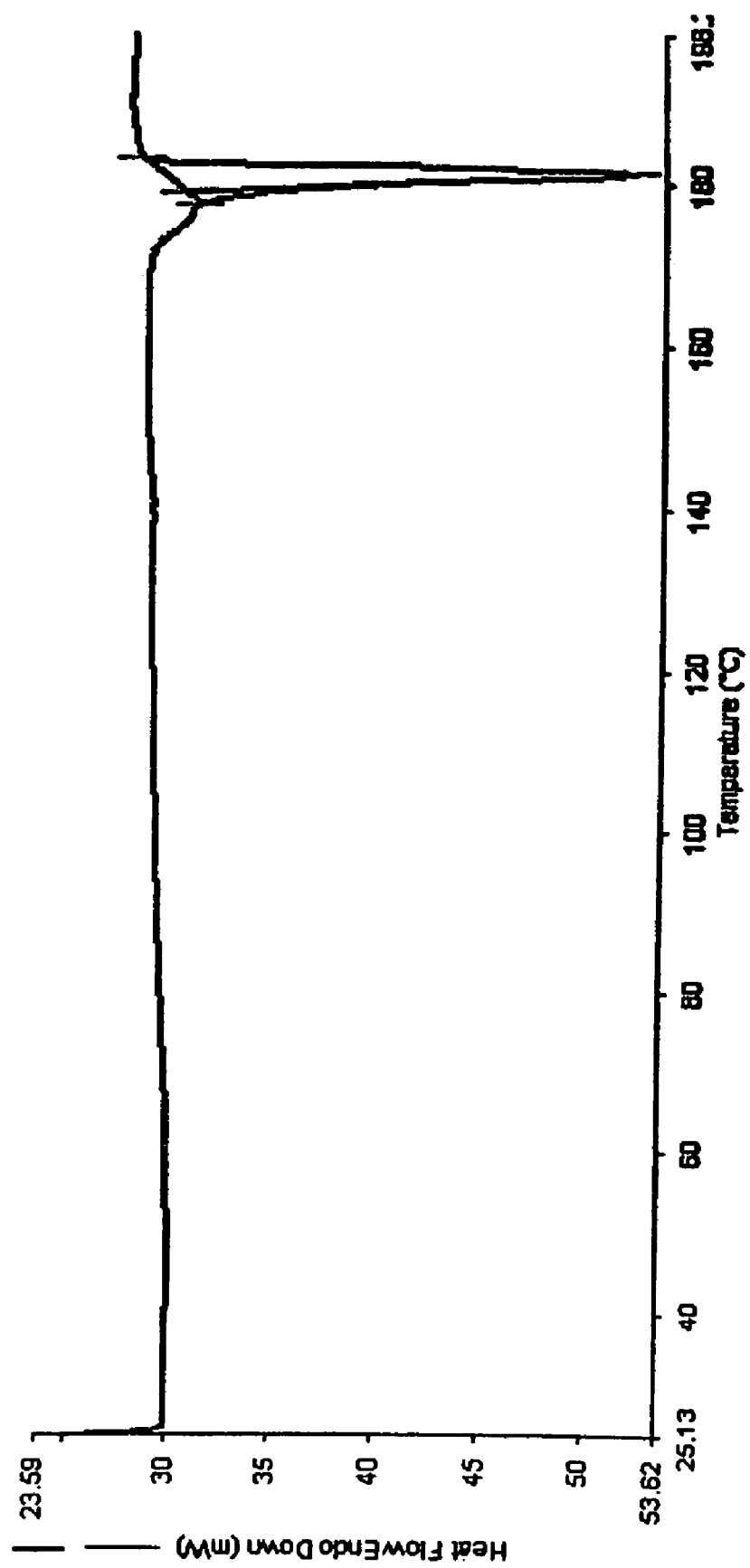
FIG. 4 depicts a DSC trace of bazedoxifene acetate form B polymorph as a comparison.

DSC measurements (see, e.g., FIGS. 3 and 4) were carried out in both sealed pan and vented pan at a scan rate of 10° C./min from 25° C. to 200° C. under nitrogen purge using a Pyris I DSC from Perkin-Elmer.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

What is claimed is:

1. A crystalline polymorph (Form A) of bazedoxifene acetate having a powder X ray diffraction pattern comprising characteristic peaks, in terms of 2θ, at about 12.7° and about 18.5°.

2. The polymorph of claim 1 wherein said powder X-ray diffraction pattern further comprises characteristic peaks, in terms of 2θ, at about 16.0, about 20.7° and about 22.3°.

3. The polymorph of claim 1 wherein said powder X-ray diffraction pattern comprises at least 5 characteristic peaks, in terms of 2θ, selected from about 9.8°, about 12.7°, about 15.2°, about 16.0°, about 17.1°, about 17.4°, about 18.5°, about 18.8°, about 19.6°, about 20.4°, about 20.7°, about 22.3°, about 23.5°, about 24.9°, about 25.6°, about 26.1°, about 27.4°, about 28.0°, about 28.7°, about 29.6°, about 29.9°, and about 30.7°.

4. The polymorph of claim 1 having a powder X-ray diffraction pattern substantially as shown in FIG. 1.

5. The polymorph of claim 1 having an infrared spectrum in KBr comprising one or more characteristic peaks selected from about 1511, about 1467, and about 1242 cm-1.

6. The polymorph of claim 1 having an infrared spectrum in KBr substantially as shown in FIG. 2.

7. The polymorph of claim 1 having a differential scanning calorimetry trace showing a maximum at about 176° C.

8. The polymorph of claim 1 having a differential scanning calorimetry trace substantially as shown in FIG. 3.

9. A solid composition comprising the polymorph of claim 1.

10. The composition of claim 9 wherein at least about 50% by weight of total bazedoxifene acetate in said composition is present as said polymorph.

11. The composition of claim 9 wherein at least about 70% by weight of total bazedoxifene acetate in said composition is present as said polymorph.

12. The composition of claim 9 wherein at least about 80% by weight of total bazedoxifene acetate in said composition is present as said polymorph.

13. The composition of claim 9 wherein at least about 90% by weight of total bazedoxifene acetate in said composition is present as said polymorph.

14. The composition of claim 9 wherein at least about 95% by weight of total bazedoxifene acetate in said composition is present as said polymorph.

15. The composition of claim 9 wherein at least about 97% %by weight of total bazedoxifene acetate in said composition is present as said polymorph.

16. The composition of claim 9 wherein at least about 98.0% by weight of total bazedoxifene acetate in said composition is present as said polymorph.

17. The composition of claim 9 wherein at least about 98.1% by weight of total bazedoxifene acetate in said composition is present as said polymorph.

18. The composition of claim 9 wherein at least about 98.2% by weight of total bazedoxifene acetate in said composition is present as said polymorph.

19. The composition of claim 9 wherein at least about 98.3% by weight of total bazedoxifene acetate in said composition is present as said polymorph.

20. The composition of claim 9 wherein at least about 98.4% by weight of total bazedoxifene acetate in said composition is present as said polymorph.

21. The composition of claim 9 wherein at least about 98.5% y weight of total bazedoxifene acetate in said composition is present as said polymorph.

22. The composition of claim 9 wherein at least about 98.6% by weight of total bazedoxifene acetate in said composition is present as said polymorph.

23. The composition of claim 9 wherein at least about 98.7% by weight of total bazedoxifene acetate in said composition is present as said polymorph.

24. The composition of claim 9 wherein at least about 98.8% by weight of total bazedoxifene acetate in said composition is present as said polymorph.

25. The composition of claim 9 wherein at least about 98.9% by weight of total bazedoxifene acetate in said composition is present as said polymorph.

26. The composition of claim 9 wherein at least about 99.0% by weight of total bazedoxifene acetate in said composition is present as said polymorph.

27. The composition of claim 9 wherein at least about 99.1% by weight of total bazedoxifene acetate in said composition is present as said polymorph.

28. The composition of claim 9 wherein at least about 99.2% by weight of total bazedoxifene acetate in said composition is present as said polymorph.

29. The composition of claim 9 wherein at least about 99.3% by weight of total bazedoxifene acetate in said composition is present as said polymorph.

30. The composition of claim 9 wherein at least about 99.4% by weight of total bazedoxifene acetate in said composition is present as said polymorph.

31. The composition of claim 9 wherein at least about 99.5% by weight of total bazedoxifene acetate in said composition is present as said polymorph.

32. The composition of claim 9 wherein at least about 99.6% by weight of total bazedoxifene acetate in said composition is present as said polymorph.

33. The composition of claim 9 wherein at least about 99.7% by weight of total bazedoxifene acetate in said composition is present as said polymorph.

34. The composition of claim 9 wherein at least about 99.8% by weight of total bazedoxifene acetate in said composition is present as said polymorph.

35. The composition of claim 9 wherein at least about 99.9% by weight of total bazedoxifene acetate in said composition is present as said polymorph.

36. A solid composition comprising said polymorph of claim 1 (Form A) and Form B.

37. The composition of claim 36 comprising about 70 to about 90% by weight of Form A and about 10 to about 30% by weight of Form B.

38. The composition of claim 36 comprising about 75 to about 85% by weight of Form A and about 15 to about 25% by weight of Form B.

39. The composition of claim 36 comprising about 78 to about 92% by weight of Form A and about 18 to about 22% by weight of Form B.

40. The composition of claim 36 comprising about 80% by weight of Form A and about 20% by weight of Form B.

41. A solid composition comprising bazedoxifene acetate wherein about 70% to about 90% by weight of total bazedoxifene acetate in said composition is present as the polymorph of claim 1 (Form A) and about 10 to about 30% by weight of total bazedoxifene acetate in said composition is present as Form B.

42. A solid composition comprising bazedoxifene acetate wherein about 75% to about 85% by weight of total bazedoxifene acetate in said composition is present as the polymorph of claim 1 (Form A) and about 15 to about 25% by weight of total bazedoxifene acetate in said composition is present as Form B.

43. A solid composition comprising bazedoxifene acetate wherein about 78% to about 82% by weight of total bazedoxifene acetate in said composition is present as the polymorph of claim 1 (Form A) and about 18 to about 22% by weight of total bazedoxifene acetate in said composition is present as Form B.

44. A solid composition comprising bazedoxifene acetate wherein about 80% by weight of total bazedoxifene acetate in said composition is present as the polymorph of claim 1 (Form A) and about 20% by weight of total bazedoxifene acetate in said composition is present as Form B.

45. A solid composition comprising the polymorph of claim 1 and a pharmaceutically acceptable carrier.

46. A solid composition consisting essentially of bazedoxifene acetate wherein at least 95% by weight of said bazedoxifene acetate is present in said composition as the polymorph of claim 1.

47. A solid composition consisting essentially of bazedoxifene acetate wherein at least 97% by weight of said bazedoxifene acetate is present in said composition as the polymorph of claim 1.

48. A solid composition consisting essentially of bazedoxifene acetate wherein at least 98.0% by weight of said bazedoxifene acetate is present in said composition as the polymorph of claim 1.

49. A solid composition consisting essentially of bazedoxifene acetate wherein at least 98.1% by weight of said bazedoxifene acetate is present in said composition as the polymorph of claim 1.

50. A solid composition consisting essentially of bazedoxifene acetate wherein at least 98.2% by weight of said bazedoxifene acetate is present in said composition as the polymorph of claim 1.

51. A solid composition consisting essentially of bazedoxifene acetate wherein at least 98.3% by weight of said bazedoxifene acetate is present in said composition as the polymorph of claim 1.

52. A solid composition consisting essentially of bazedoxifene acetate wherein at least 98.4% by weight of said bazedoxifene acetate is present in said composition as the polymorph of claim 1.

53. A solid composition consisting essentially of bazedoxifene acetate wherein at least 98.5% by weight of said bazedoxifene acetate is present in said composition as the polymorph of claim 1.

54. A solid composition consisting essentially of bazedoxifene acetate wherein at least 98.6% by weight of said bazedoxifene acetate is present in said composition as the polymorph of claim 1.

55. A solid composition consisting essentially of bazedoxifene acetate wherein at least 98.7% by weight of said bazedoxifene acetate is present in said composition as the polymorph of claim 1.

56. A solid composition consisting essentially of bazedoxifene acetate wherein at least 98.8% by weight of said bazedoxifene acetate is present in said composition as the polymorph of claim 1.

57. A solid composition consisting essentially of bazedoxifene acetate wherein at least 98.9% by weight of said bazedoxifene acetate is present in said composition as the polymorph of claim 1.

58. A solid composition consisting essentially of bazedoxifene acetate wherein at least 99.0% by weight of said bazedoxifene acetate is present in said composition as the polymorph of claim 1.

59. A solid composition consisting essentially of bazedoxifene acetate wherein at least 99.1% by weight of said bazedoxifene acetate is present in said composition as the polymorph of claim 1.

60. A solid composition consisting essentially of bazedoxifene acetate wherein at least 99.2% by weight of said bazedoxifene acetate is present in said composition as the polymorph of claim 1.

61. A solid composition consisting essentially of bazedoxifene acetate wherein at least 99.3% by weight of said bazedoxifene acetate is present in said composition as the polymorph of claim 1.

62. A solid composition consisting essentially of bazedoxifene acetate wherein at least 99.4% by weight of said bazedoxifene acetate is present in said composition as the polymorph of claim 1.

63. A solid composition consisting essentially of bazedoxifene acetate wherein at least 99.5% by weight of said bazedoxifene acetate is present in said composition as the polymorph of claim 1.

64. Amended) A solid composition consisting essentially of bazedoxifene acetate wherein at least 99.6% by weight of said bazedoxifene acetate is present in said composition as the polymorph of claim 1.

65. A solid composition consisting essentially of bazedoxifene acetate wherein at least 99.7% by weight of said bazedoxifene acetate is present in said composition as the polymorph of claim 1.

66. A solid composition consisting essentially of bazedoxifene acetate wherein at least 99.8% by weight of said bazedoxifene acetate is present in said composition as the polymorph of claim 1.

67. A solid composition consisting essentially of bazedoxifene acetate wherein at least 99.9% by weight of said bazedoxifene acetate is present in said composition as the polymorph of claim 1.

68. A solid composition comprising the polymorph of claim 1 and one or more steroidal estrogens selected from the group consisting of mestranol and ethynyl estradiol.

69. A method of preparing bazedoxifene acetate polymorphic Form A comprising:
  a) reacting hexamethyleneimino benzyloxyindole with a hydrogenating reagent in a solvent and optionally in the presence of a hydrogenation catalyst for a time and under conditions suitable for forming a reaction mixture comprising bazedoxifene free base;
  b) treating said reaction mixture with acetic acid for a time and under conditions suitable for forming bazedoxifene acetate polymorph Form A.

70. The method of claim 69 wherein said solvent comprises an alcohol.

71. The method of claim 70 wherein said alcohol comprises ethanol.

72. The method of claim 69 wherein said solvent farther comprises ethyl acetate.

73. The method of claim 69 wherein said hydrogenating reagent is $H_2$.

74. The method of claim 69 wherein said hydrogenating catalyst is Pd/C.

75. The method of claim 69 wherein said treating of step b) is carried out in the presence of an antioxidant.

76. The method of claim 75 wherein said antioxidant is ascorbic acid.

77. The method of claim 69 wherein said treating of step b) is carried out at a temperature of about 25° C. or lower.

78. The method of claim 69 further comprising maintaining the reaction mixture of step b) at a temperature of about −20 to about 20° C. for at least about 2 hours.

79. The method of claim 69 further comprising maintaining the reaction mixture of step b) at a temperature of about 20° C. for at least about 2 hours.

80. The method of claim 69 further comprising maintaining the reaction mixture of step b) at a temperature of about 0° C. for at least about 2 hours.

81. A method of preparing bazedoxifene acetate polymorphic Form A comprising crystallizing bazedoxifene acetate from a solution comprising an alcohol wherein said solution is maintained at a temperature below about 20° C.

82. The method of claim 81 wherein said solution is maintained at a temperature below about 10° C.

83. The method of claim 81 wherein said alcohol comprises ethanol.

84. A method of lowering cholesterol in a mammal comprising administering to said mammal a therapeutically effective amount of the polymorph of claim 1.

85. A method of inhibiting bone loss in a mammal comprising administering to said mammal a therapeutically effective amount of the solid polymorph of claim 1.

86. A method of treating breast cancer in a mammal comprising administering to said mammal a therapeutically effective amount of the polymorph of claim 1.

87. A method of treating a postmenopausal woman for one or more vasomotor disturbances comprising administering to said postmenopausal woman a therapeutically effective amount of the solid polymorph of claim 1.

88. The method of claim 87 wherein the vasomotor disturbance is hot flush.

89. The crystalline polymorph Form A of bazedoxifene acetate prepared by the method of the polymorph of claim 1.

90. The polymorph of claim 1 prepared by the method comprising:
  a) reacting hexamethyleneimino benzyloxyindole with a hydrogenating reagent in a solvent and optionally in the presence of a hydrogenation catalyst for a time and under conditions suitable for forming a reaction mixture comprising bazedoxifene free base;
  b) treating said reaction mixture with acetic acid for a time and under conditions suitable for forming bazedoxifene acetate polymorph Form A.

91. The polymorph of claim 1 prepared by the method comprising crystallizing bazedoxifene acetate from a solution comprising an alcohol wherein said solution is maintained at a temperature below about 20° C.

* * * * *